United States Patent
Petschen et al.

(10) Patent No.: US 7,829,726 B2
(45) Date of Patent: Nov. 9, 2010

(54) METHOD FOR MANUFACTURING IMIDAZOLE COMPOUNDS AND SALTS AND PSEUDOPOLYMORPHS THEREOF

(75) Inventors: Inés Petschen, Barcelona (ES); Xavier Camps, Barcelona (ES); Juan Sallarés, Sant Cugat (ES)

(73) Assignee: Ferrer Internacional, S.A, Barcelona (ES)

( * ) Notice: Subject to any disclaimer, the term of this patent is extended or adjusted under 35 U.S.C. 154(b) by 442 days.

(21) Appl. No.: 11/662,256

(22) PCT Filed: Sep. 13, 2005

(86) PCT No.: PCT/EP2005/009825

§ 371 (c)(1),
(2), (4) Date: Jun. 5, 2008

(87) PCT Pub. No.: WO2006/029812

PCT Pub. Date: Mar. 23, 2006

(65) Prior Publication Data

US 2009/0005573 A1    Jan. 1, 2009

(30) Foreign Application Priority Data

Sep. 13, 2004 (ES) ................................ 200402183

(51) Int. Cl.
*C07D 409/12* (2006.01)
(52) U.S. Cl. .................................................. 548/311.4
(58) Field of Classification Search ............... 548/311.4
See application file for complete search history.

(56) References Cited

U.S. PATENT DOCUMENTS 5,135,943 A * 8/1992 Foguet et al. ............... 514/397
5,939,555 A   8/1999 Foguet et al.

FOREIGN PATENT DOCUMENTS

| CN | 1 358 719 A | 7/2002 |
| EP | 8 504 779 A1 | 7/1985 |
| EP | 0 151 477 A | 8/1985 |
| EP | 0 748 806 A | 12/1996 |

OTHER PUBLICATIONS

Chem. Abstract XP002354831, 2003.

* cited by examiner

*Primary Examiner*—Rei-tsang Shiao
(74) *Attorney, Agent, or Firm*—Birch, Stewart, Kolasch & Birch, LLP

(57) ABSTRACT

The invention relates to a method for manufacturing sertaconazole mononitrate. The invention also relates tesertaconazole mononitrate that is characterized by it: particle size and to sertaconazole mononitrate monohydrate.

6 Claims, 5 Drawing Sheets

Formula chart

Sertaconazole mononitrate (I)

(II)

(III)

(IV, Z = Cl, HO$_4$S)

Sertaconazole mononitrate monohydrate (V)

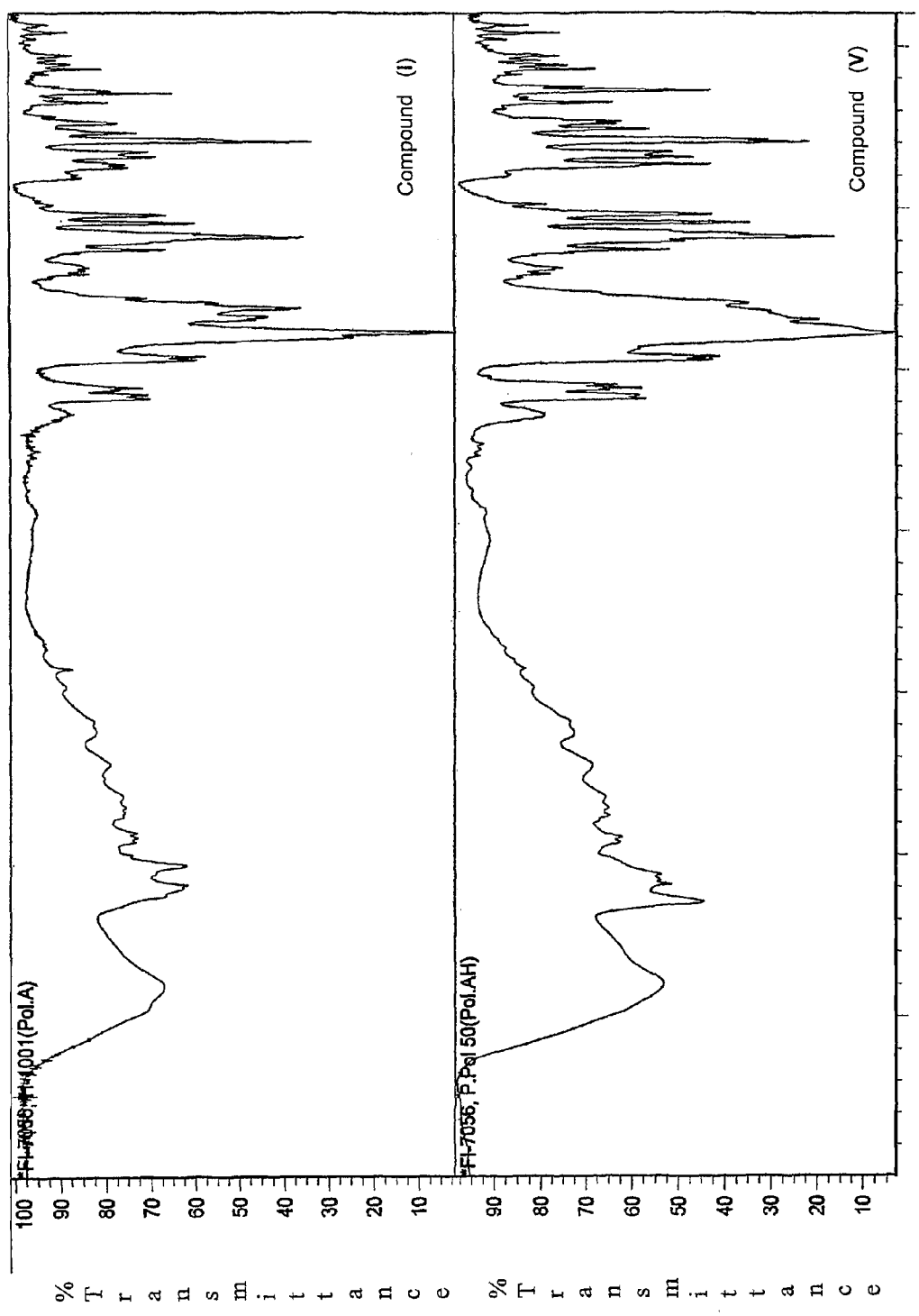
Fig. 2 IR spectrum of sertaconazole mononitrate monohydrate (V) and sertaconazole mononitrate (I)

Fig. 3    DSC of sertaconazole mononitrate monohydrate (V) and sertaconazole mononitrate (I)
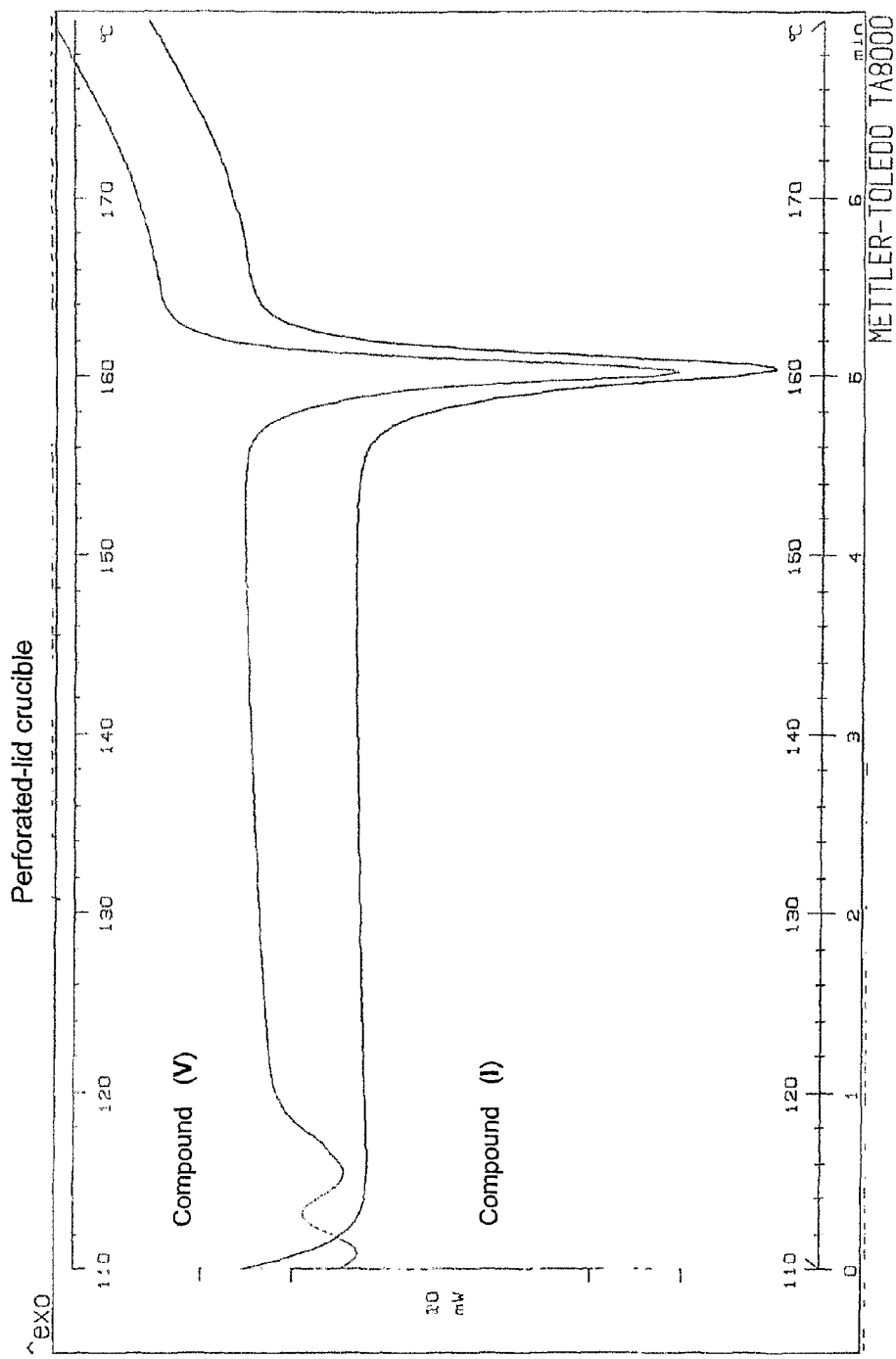

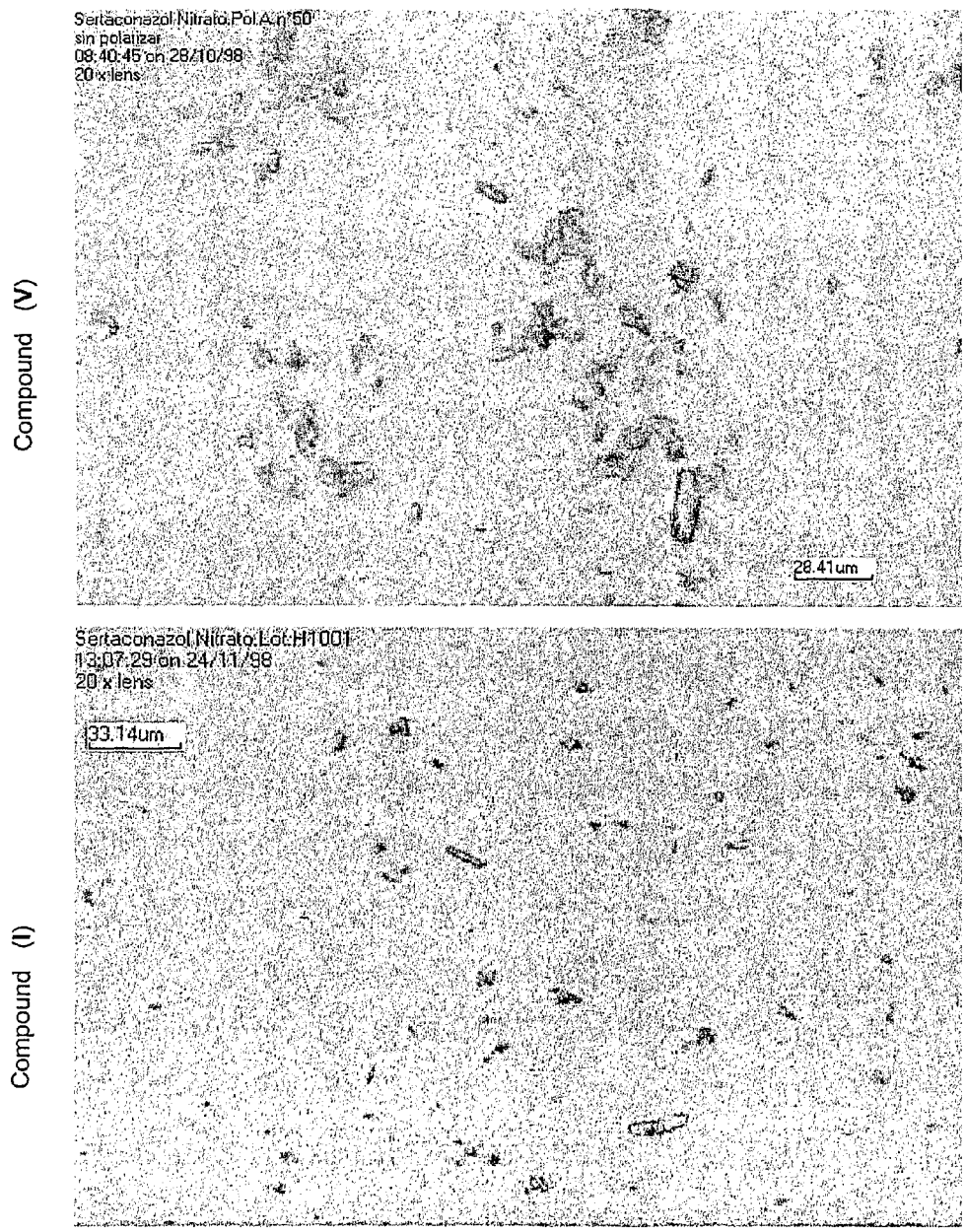
Fig. 4 Microphotographies of sertaconazole mononitrate monohydrate (V) and sertaconazole mononitrate (I)

Fig. 5  X-ray diffractogram of sertaconazole mononitrate monohidrate (V) and sertaconazole mononitrate (I)
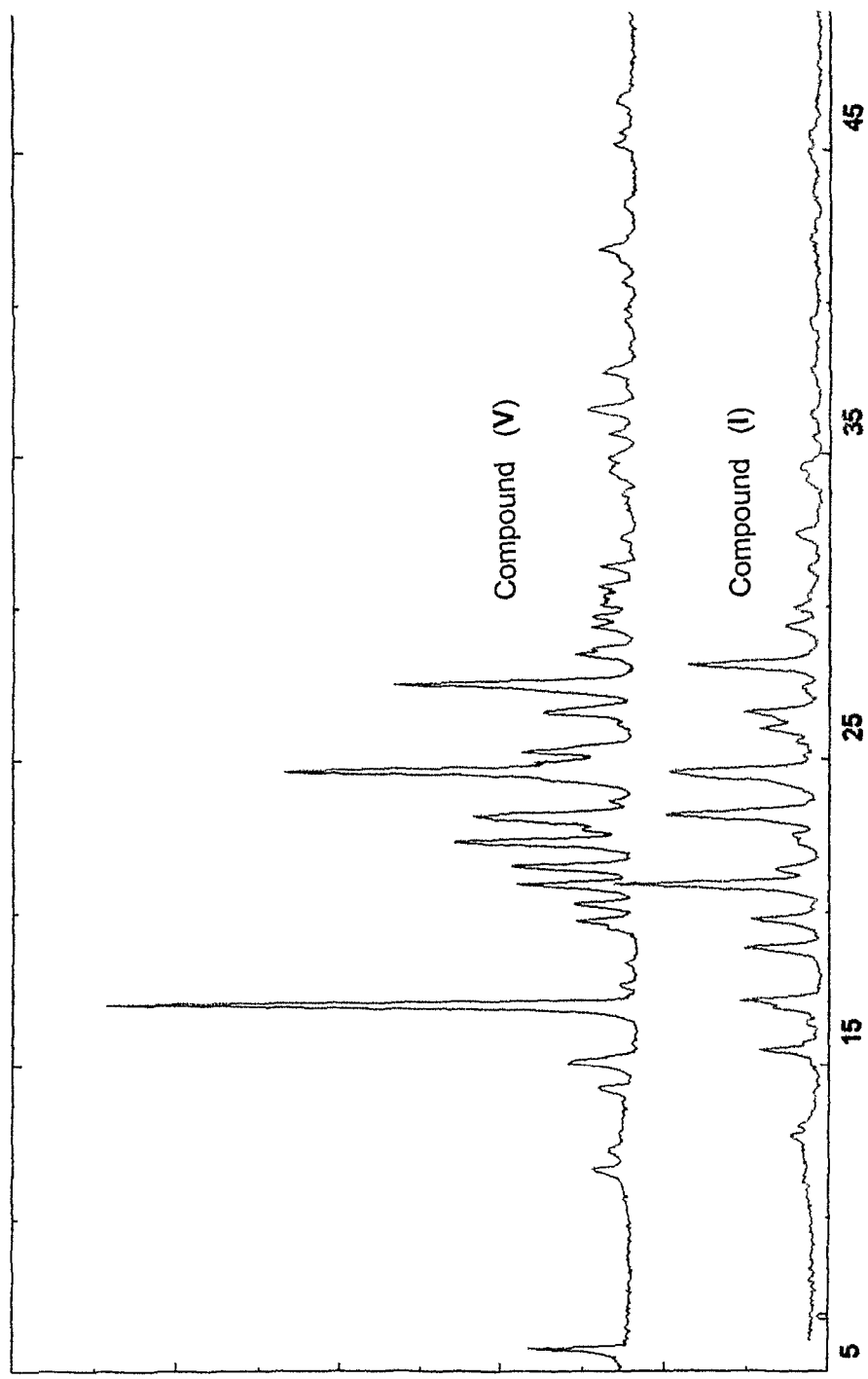

METHOD FOR MANUFACTURING IMIDAZOLE COMPOUNDS AND SALTS AND PSEUDOPOLYMORPHS THEREOF

FIELD OF THE INVENTION

The present invention relates to a method for manufacturing imidazole compounds, namely sertaconazole, and salts and pseudopolymorphs thereof.

BACKGROUND OF THE INVENTION

Sertaconazole (WHO-INN) is an antifungal agent broadly used in the therapy of infections caused by fungi and yeasts in man and animals. Sertaconazole refers to 1-[2-(7-chlorobenzo[b]thiophene-3-yl-methoxy)-2-(2,4-dichloro-phenyl)ethyl]-1H-imidazole. Commonly sertaconazole is used as mononitrate salt (I).

The specification EP 151477 discloses the preparation of sertaconazole mononitrate (I) by reacting 1-(2,4-dichlorophenyl)-2-(1H-imidazol-1-yl)-ethanol (II) with sodium hydride and 3-bromomethyl-7-chlorobenzo[b]thiophene (III) in hexamethylphosphoramide (HMPA) and treating the resulting sertaconazole free base with nitric acid.

The specification CN 1358719 (CAPLUS 2003:711267) discloses the synthesis of sertaconazole mononitrate (I) by etherifying 3-bromomethyl-7-chlorobenzo[b]thiophene (III) with 1-(2,4-dichlorophenyl)-2-(1H-imidazol-1-yl)-ethanol (II) at a molar ratio of 1:1 in toluene-water (3:1, v/v) in the presence of sodium hydroxide and 50% tetrabutylammonium chloride (IV, Z=Cl) solution at 80° C. for 4 hours, extracting with ethyl ether to obtain free base of sertaconazole, salifying with nitric acid and recrystallizing in 95% ethanol. The resulting content in sertaconazole mononitrate of the thus prepared product is >98.5%.

Molecular formulas for compounds (I)-(IV) and sertaconazole mononitrate monohydrate (V) are shown in FIG. 1/5.

BRIEF DESCRIPTION OF THE DRAWINGS

FIG. 2: Infrared (IR) spectrum of sertaconazole mononitrate monohydrate (V) compared to sertaconazole mononitrate (I).

FIG. 3: The recorded Differential Scanning Calorimettry (DSC) of sertaconazole mononitrate monohydrate (V) compared to sertaconazole mononitrate (I).

FIG. 4: Sertaconazole mononitrate monohydrate (V) and sertaconazole mononitrate (I) microphotographs.

FIG. 5: The X ray diffractograms of sertaconazole mononitrate monohydrate (V) and sertaconazole mononitrate (I).

DESCRIPTION

Figure 1:
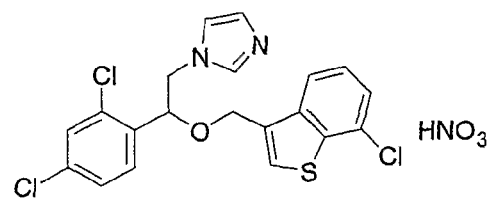
FIG. 1: Molecular formulas for sertaconazole mononitrate (I), 1-(2,4-dichlorophenyl)-2-(1H-imidazol-1-yl)-ethanol (II), 3-bromomethyl-7-chlorobenzo[b]thiophene (III), tetrabutylammonium chloride (IV) and sertaconazole mononitrate monohydrate (V).
Figure 1:
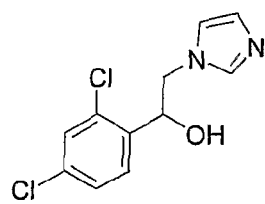
Figure 1:
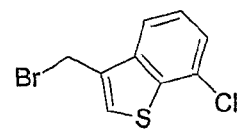
Figure 1:
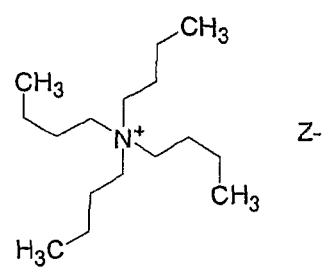
Figure 1:
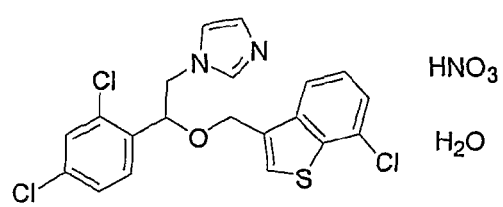

The present invention relates to a new chemical process for the preparation of sertaconazole mononitrate (I).

More specifically, the invention involves a process for the preparation of sertaconazole mononitrate (I) which is more efficient than those disclosed in EP 151477 and CN 1358719, and which can surprisingly provide sertaconazole mononitrate (I) of a clinical quality standard (>99.5%). In this context, sertaconazole mononitrate (I) of a clinical quality standard means material of sufficient purity for administration to humans. The particle size of the product thus obtained is 10 μm or less for at least 40% (v:v) of the whole sample and 30 μm or less for at least 95% (v:v) of the whole sample, which constitutes a suitable material to be used directly in pharmaceutical preparations.

In contrast to the specification EP 151477, the process of the present invention avoids the use of hazardous solvents such as hexamethylphosphoramide, known as chemical mutagen (The Merck Index, page 844, 13$^{th}$ Edition, 2001, Merck & Co., Inc.), and ethyl ether, known as a highly flammable and explosive liquid (ibid, page 677).

Moreover, the process in the present invention is much more efficient than that disclosed in the specification of CN 1358719 (CAPLUS 2003:711267), because the stoichiometric amounts of starting reactants needed to obtain 1000 g of final sertaconazole mononitrate (I) are lower than the amounts used in CN 1358719 (Table 1).

TABLE 1

Major stoichiometric differences for obtaining 1000 g of sertaconazole mononitrate (I)

| Substance | Present invention | CN 1358719 |
|---|---|---|
| Reactant (II), {1-(2,4-Dichlorophenyl)-2-(1H-imidazol-1-yl)-ethanol} | 2.40 mol | 3.39 mol |
| Reactant (III), {3-bromomethyl-7-chlorobenzo[b]thiophene} | 2.62 mol | 3.39 mol |
| Catalyst (IV, Z = HSO$_4$, Cl) {Tetrabutylammonium} | 0.121 mol {Z = HSO$_4$} | 0.488 mol {Z = Cl} |
| Molar ratio IV:II | 0.050 | 0.144 |

The key step in the overall process involves the dehydration of the immediate precursor, sertaconazole mononitrate monohydrate (V), to sertaconazole mononitrate (I).

Sertaconazole mononitrate monohydrate (V) has not been disclosed previously and also forms part of the invention. Sertaconazole mononitrate monohydrate (V) can also be called sertaconazole mononitrate pseudopolymorph.

In a preferred embodiment, the dehydration is carried out in a mixture of ethanol and water at 75-80° C., and slowly adding (6-8 hours) this solution over an aqueous solution of nitric acid cooled at 5-15° C., filtering, drying at 60-70° C., sieving and finally drying at 80-90° C. Sertaconazole mononitrate (I) so obtained has the sufficient purity and the proper particle size to be used directly in pharmaceutical preparations. The preparation of sertaconazole mononitrate monohydrate (V) comprises in a first step the reaction of 1-(2,4-dichlorophenyl)-2-(1H-imidazol-1-yl)-ethanol (II) with an excess of 3-bromomethyl-7-chlorobenzo[b]thiophene (III) in the presence of tetrabutylammonium hydrogen sulfate (IV, Z=HO$_4$S) and sodium hydroxide in toluene at 30-45° C., followed by the addition of water, cooling the mixture to a mass temperature of 0-15° C. and filtering, washing the solid material obtained with water and toluene, and refluxing the sertaconazole free base obtained in absolute ethanol until complete dissolution, heating the mass at 60-80° C. and adding water, further cooling at 5-15° C., filtering the solid material formed and washing it with a mixture of ethanol and water, re-dissolving the pure sertaconazole free base obtained in absolute ethanol at 70-80° C., cooling the mixture at a mass temperature of 65-75° C. and thereafter adding a solution containing 60% nitric acid in water, maintaining the temperature for 10-20 minutes, keeping the pH below 2, cooling the mixture at 5-15° C. and maintaining this temperature from 30 minutes to 2 hours, followed by filtering and washing to yield sertaconazole mononitrate monohydrate (V).

In another embodiment, the molar ratio of reactant II reactant III is from 0.85 to 0.95.

In another embodiment, the molar ratio of the catalyst (IV, Z=HSO$_4$):limiting reactant (II) is from 0.025 to 0.060.

In another embodiment, the molar ratio of the catalyst (IV, Z=HSO$_4$):limiting reactant (II) is from 0.045 to 0.055.

In a more preferred embodiment, the molar ratio of the catalyst (IV, Z=HSO$_4$):limiting reactant (II) is 0.050.

Pharmaceutical compositions stand for topical preparations such as bath additives, creams, gels, ointments, cutaneous pastes, medicated plasters, cutaneous foams, shampoos, solutions for cutaneous sprays, suspensions for cutaneous sprays, powders for cutaneous sprays, cutaneous liquids, cutaneous solutions, cutaneous suspensions, cutaneous emulsions, cutaneous powders, transdermal patches, collodions, medicated nail lacquers, poultices, cutaneous sticks, cutaneous sponges, impregnated dressings, and the like; vaginal preparations such as vaginal creams, vaginal gels, vaginal ointments, vaginal foams, vaginal solutions, vaginal suspensions, vaginal emulsions, tablets for vaginal solution, pessaries, hard vaginal capsules, soft vaginal capsules, vaginal tablets, effervescent vaginal tablets, medicated vaginal tampons, vaginal delivery systems, and the like; oromucosal preparations such as gargles, concentrates for gargles, powders for gargle solutions, tablets for gargle solutions, oromucosal solutions, oromucosal suspensions, oromucosal drops, oromucosal sprays, sublingual sprays, mouth washes, tablets for mouth wash solutions, gingival solutions, oromucosal gels, oromucosal pastes, gingival gels, gingival pastes, sublingual tablets, muco-adhesive buccal tablets, buccal tablets, lozenges, compressed lozenges, pastilles, an the like; dental preparations such as dental gels, dental sticks, dental inserts, dental powders, dental solutions, dental suspensions, dental emulsions, toothpastes, and the like.

Another embodiment of the present invention is sertaconazole mononitrate (I) characterized by a particle size of 10 μm or less for at least 40% of the whole sample and 30 μm or less for at least 95% of the whole sample.

Another embodiment of the present invention is sertaconazole mononitrate monohydrate (V).

The present invention will now be described in more detail with reference to the following examples. The technical scope of the present invention is not limited to these examples.

EXAMPLE 1

Sertaconazole Mononitrate Monohydrate (V) (Sertaconazole Mononitrate Pseudopolymorph)

A 2-L flask was loaded with 308 mL of toluene, 100 g of 1-(2,4-dichlorophenyl)-2-(1H-imidazol-1-yl)-ethanol (II) (0.389 mol) and 6.67 g of tetrabutylammonium hydrogen sulfate (IV, Z=HSO$_4$) (0.0196 mol). Then, 155 g of sodium hydroxide (purity 49%; 1.905 mol) were added. The mixture was heated at 35-40° C. and stirred for 15 minutes. A solution comprising 111.11 g of 3-bromomethyl-7-chlorobenzo[b]thiophene (III) (0.425 mol) and 595 mL of toluene, maintaining the mass temperature between 37 and 40° C., was added for at least 30 minutes. After the addition, the system was maintained between 37 and 40° C. for 2.5 hours and thereafter water (635 mL) was added. The mixture was cooled to a mass temperature of 5-10° C. and the sertaconazole precipitated was filtered and washed with water and cold toluene (5-10° C.), obtaining 179.7 g of wet sertaconazole free base (161.7 g dry).

The sertaconazole free base obtained was loaded into a 2 L reactor containing 848 mL of absolute ethanol. The mixture was refluxed until complete dissolution. Then the mixture was heated at a mass temperature between 68 and 72° C., and 236 mL of water were added. The mixture was cooled at 10° C. and this temperature was maintained for 1 hour. The solid material formed was filtered and washed with a solution of 160 mL of absolute ethanol and 51 mL of water previously cooled at 10° C. Wet pure sertaconazole free base (177.9 g) was obtained (158 g dry). The obtained pure sertaconazole free base was loaded into a 2 L reactor and re-dissolved with 932 mL of absolute ethanol at 75° C. The mixture was then cooled at a mass temperature of 67-70° C. and a solution containing 53.7 g (0.512 mol) of 60% nitric acid in 193 mL of water is added. The temperature was stabilized for 15 minutes, checking that the pH was maintained below 2. The mixture was cooled at 10° C. and kept for 1 hour. The precipitated material was filtered and washed with water, providing 215.9 g of sertaconazole mononitrate monohydrate (V)(Sertaconazole mononitrate pseudopolymorph). Yield 88.7%.

Analytical Data

IR (infrared): A Magna-IR 550 Nicolet spectrometer with a database running in Omnic 2.1 software has been used. The recorded IR spectrum of sertaconazole mononitrate monohydrate (V) compared to sertaconazole mononitrate (I) is shown in FIG. 2/5.

DSC (differential scanning calorimetry): A Mettler TA-8000 instrument comprising DSC-820 and TG-50 components, and a MT-5 balance provided with a database running in TAS 810 1.1 software has been used. A product sample of 1 to 5 mg was weighted in a 40 μL aluminum crucible, maintaining the following conditions:

Temperature range: 110-180° C.

Heating speed: 10° C./min

Nitrogen flow: 100 mL/min

The recorded DSC of sertaconazole mononitrate monohydrate (V) compared to sertaconazole mononitrate (I) is shown in FIG. 3/5.

Microscopy: A Nikon-Eclipse E-600 unit with polarized light, provided with a Linkam THMS 600 heating plate and a Linksys database and image manager software has been used. Some product particles were suspended in mineral oil on a glass slide and the sample was examined by magnification depending on the particle size and using polarized light or not.

Sertaconazole mononitrate monohydrate (V) and sertaconazole mononitrate (I) microphotographs are shown in FIG. 4/5.

X Rays Diffraction: A Siemens powder X Ray Diffraction Equipment model D-500 has been used.

The X Rays diffractograms for sertaconazole mononitrate monohydrate (V) and sertaconazole mononitrate (I) are shown in FIG. 5/5. The crystal data and structure refinement for sertaconazole mononitrate monohydrate (V) are shown in Table 2.

TABLE 2

Crystal data and structure refinement for sertaconazole mononitrate monohydrate (V)

| | |
|---|---|
| Empirical formula | $C_{20}H_{15}Cl_3N_2OS \cdot HNO_3 \cdot H_2O$ |
| Formula weight | 518.78 |
| Temperature | 293(2)° K |
| Wavelength | 0.71069 Å |
| Crystal system | Monoclinic |
| Space group | P2$_1$/c |
| | a = 16.049(2)Å    α = 90° |

TABLE 2-continued

Crystal data and structure refinement for sertaconazole mononitrate monohydrate (V)

| | |
|---|---|
| Unit cell dimensions | b = 8.946(7)Å   β = 102.046(7)° |
| | c = 15.990(3)Å   γ = 90° |
| Volume | 2245(2) Å$^3$ |
| Z | 4 |
| Density (calculated) | 1.535 Mg/m$^3$ |
| Absorption coefficient | 0.540 mm$^{-1}$ |
| Crystal size | 0.1 × 0.1 × 0.2 mm |
| Theta range for data collection | 1.30 to 30.07° |
| Index ranges | −3 ≦ h ≦ 16, |
| | −12 ≦ k ≦ 12, |
| | −22 ≦ l ≦ 21 |
| Reflections collected | 11440 |
| Independent reflections | 5861 [R(int) = 0.1748] |
| Refinement method | Full-matrix least-squares on F$^2$ |
| Data/restraints/parameters | 3246/1/336 |
| Goodness-of-fit on F$^2$ | 0.980 |
| Final R indices [I > 2σ(I)] | R$_1$ = 0.0644, WR$_2$ = 0.1302 |
| R indices (all data) | R$_1$ = 0.3270, WR$_2$ = 0.2365 |
| Extinction coefficient | 0.0000(6) |
| Largest diff. peak and hole | 0.356 and −0.429 e.Å$^3$ |

EXAMPLE 2

Sertaconazole Mononitrate (I)

Sertaconazole mononitrate monohydrate (V) (215.9 g 0.344 mol) obtained according to the previous description was dissolved in 991 mL of absolute ethanol and 150 mL of water. The mixture was heated at 75-80° C. and then added over another solution comprising 2.8 L of water and 1.7 g of 60% nitric acid which has been cooled at 10° C. for approximately 6-8 hours. Having finished the addition, the mixture was stirred for 15 minutes at 10° C. The material obtained was filtered, dried at 65° C., sieved and finally dried at 85° C., providing 162.2 g of sertaconazole mononitrate (I). Yield 93.9%. Global yield 83.3%. The particle size was 10 μm for 40% of the whole sample and 30 μm for 95% of the whole sample. MP 158-160° C. The resulting content in sertaconazole mononitrate of the prepared product was >99.5%.

The invention claimed is:

1. A method for manufacturing sertaconazole mononitrate (I) which comprises:
   (i) the reaction of 1-(2,4-dichlorophenyl)-2-(1H-imidazol-1-yl)-ethanol (II) with 3-bromomethyl-7-chlorobenzo[b] thiophene (III) in the presence of tetrabutylammonium hydrogen sulfate (IV, Z=HSO$_4$) and sodium hydroxide in toluene at 30-45° C., followed by addition of water, cooling the mixture to a mass temperature of 0-15° C. and then filtering, washing the solid material obtained with water and toluene, and refluxing the sertaconazole free base thus obtained in absolute ethanol until complete dissolution, heating the mass at 60-80° C. and adding water, further cooling at 5-15° C., filtering the solid material formed and washing with a mixture of ethanol and water, re-dissolving the obtained pure sertaconazole free base in absolute ethanol at 70-80° C., cooling the mixture at a mass temperature of 65-75° C. and thereafter adding a solution containing 60% nitric acid in water, maintaining the temperature for 10-20 minutes, keeping the pH below 2, cooling the mixture at 5-15° C. and maintaining this temperature during 30 minutes to 2 hours, followed by filtering and washing to yield sertaconazole mononitrate monohydrate (V); and
   (ii) dissolving sertaconazole mononitrate monohydrate in a mixture of ethanol and water, heating the mass at 75-80° C., adding the mixture over an aqueous solution of nitric acid cooled at 5-15° C., filtering, drying at 60-70° C., sieving and finally drying at 80-90° C.

2. The method according to claim 1 wherein the molar ratio of reactant II: reactant III is from 0.85 to 0.95.

3. The method according to claim 1 wherein the molar ratio of the catalyst (IV, Z=HSO$_4$): limiting reactant (II) is from 0.025 to 0.060.

4. The method according to claim 3 wherein the molar ratio of the catalyst (IV, Z=HSO$_4$): limiting reactant (II) is from 0.045 to 0.055.

5. The method according to claim 3 wherein the molar ratio of the catalyst (IV, Z=HSO$_4$): limiting reactant (II) is 0.050.

6. Sertaconazole mononitrate monohydrate (V).

* * * * *